United States Patent
Dementienko et al.

(10) Patent No.: US 9,919,127 B2
(45) Date of Patent: Mar. 20, 2018

(54) METHOD AND APPARATUS FOR IMPROVING SLOW WAVE SLEEP STAGE

(71) Applicant: Tessonics Corporation, Birmingham, MI (US)

(72) Inventors: Valery V. Dementienko, Moscow (RU); Roman G. Maev, Windsor (CA); Alexander S. Bugaev, Moscow (RU); Peter Indursky, Moscow (RU); Viacheslav V. Markelov, Moscow (RU); Viacheslav M. Shakhnarovich, Moscow (RU); Emil E. Strumban, West Bloomfield, MI (US)

(73) Assignee: DREAMSTONE, INC., Windsor (CA)

( * ) Notice: Subject to any disclaimer, the term of this patent is extended or adjusted under 35 U.S.C. 154(b) by 0 days.

(21) Appl. No.: 15/066,714

(22) Filed: Mar. 10, 2016

(65) Prior Publication Data
US 2017/0259029 A1 Sep. 14, 2017

(51) Int. Cl.
- *A61M 21/02* (2006.01)
- *A61N 1/36* (2006.01)
- *A61M 21/00* (2006.01)

(52) U.S. Cl.
CPC ......... *A61M 21/02* (2013.01); *A61N 1/36014* (2013.01); *A61M 2021/0072* (2013.01); *A61M 2205/3303* (2013.01); *A61M 2230/65* (2013.01)

(58) Field of Classification Search
CPC ... A61B 5/4812; A61B 5/0205; A61B 5/0476; A61B 5/4815; A61B 5/4836;
(Continued)

(56) References Cited

U.S. PATENT DOCUMENTS

2006/0206174 A1* 9/2006 Honeycutt ............... A61N 2/02
607/88
2011/0112590 A1* 5/2011 Wu ....................... A61B 5/4812
607/2
(Continued)

FOREIGN PATENT DOCUMENTS

RU 2431508 C1 10/2011
RU 2553185 C1 6/2015

OTHER PUBLICATIONS

Indursky PA, Markelov VV, Shakhnarovich VM, Dorokhov VB. Low-Frequency Rhythmic Electrocutaneous Hand Stimulation during Slow-Wave Night Sleep: Physiological and Therapeutic Effects. Human Physiology, 2013, vol. 39, pp. 642-654.*
(Continued)

*Primary Examiner* — Christine H Matthews
*Assistant Examiner* — Joshua D Lannu
(74) *Attorney, Agent, or Firm* — Carlson, Gaskey & Olds, P.C.

(57) ABSTRACT

A method and apparatus is disclosed for slow wave sleep improvement. The method includes recording a biosignal from a skin area of a patient using an electrode system. The slow wave stage of NREM sleep is detected by analyzing an oscillation rate of the biosignal. If the slow wave stage is detected, threshold electrocutaneous stimulation is applied to improve the quality of sleep. The described embodiment relates to an apparatus for slow wave sleep improvement comprising an electrode system, a measuring unit, a therapy unit and a processor. The processor is coupled to the measurement unit for receiving the biosignal corresponding to the electrodermal activity. The processor proceses the biosignal to determine the slow wave sleep stage and activates the therapy unit to deliver threshold electrocuta-
(Continued)

neous therapy to the patient with the purpose of improving the slow wave sleep stage.

26 Claims, 4 Drawing Sheets

(58) Field of Classification Search
CPC ... A61B 5/1118; A61B 5/4809; A61B 5/7264; A61B 5/04; A61B 5/4806; A61N 1/0529; A61N 1/36078; A61N 1/36185; A61N 1/0456
See application file for complete search history.

(56) References Cited

U.S. PATENT DOCUMENTS

2012/0251989 A1* 10/2012 Wetmore .............. A61M 21/00 434/236
2012/0271190 A1* 10/2012 Mortensen ........... A61B 5/0488 600/546

OTHER PUBLICATIONS

P.A. Indursky, "Low-Frequency Rhythmic Electrocutaneous Hand Stimulation during Slow-Wave Night Sleep: Physiological and Therapeutic Effects", ISSN 0362-1197, Human Physiology, 2013, vol. 39, No. 6, pp. 642-654. Pleiades Publishing, Inc., 2013.

* cited by examiner

METHOD AND APPARATUS FOR IMPROVING SLOW WAVE SLEEP STAGE

BACKGROUND

Sleep is a naturally recurring state characterized by reduced or absent consciousness, relatively suspended sensory activity, and inactivity of nearly all voluntary muscles. Sleep architecture refers to the basic structural organization of normal sleep.

There are two distinct states that alternate in 90 minute cycles and reflect differing levels of brain activity. Each sleep cycle consists of non-rapid eye movement (NREM) and rapid eye movement (REM) activities, both states repeat over and over again during a night's sleep. NREM sleep is further subdivided into four stages. Each state is characterized by a different type of brain wave.

Stage N1 is of light sleep, which is considered a transition between wakefulness and sleep and usually accounts for 5-10% of total sleep time. This stage is characterized by alpha brain waves having a frequency 8-13 Hz. An individual can be easily awakened during this period.

Stage N2 occurs throughout the sleep period and represents 40-50% of the total sleep time. This stage is characterized by theta brain waves ranging from 4 to 8 Hz. During stage N2, brain waves slow down with occasional bursts of rapid waves.

Stages III and IV are distinguished from each other only by the percentage of delta wave activity with a frequency oscillation between 0 and 4 Hz. Together these two stages represent up to 20% of total sleep time. Stages N3 and N4 represent deep sleep, during which all eye and muscle movement ceases. It is difficult to wake up an individual during these 2 stages; these have been combined by the American Academy of Sleep Medicine as stage N3 and are called slow wave or delta sleep. Slow wave sleep provides the most recuperative effect and defines the quality of sleep.

SUMMARY

According to a method described herein, the slow wave sleep stage of a patient is improved by detecting slow wave sleep stage and employing gentle, subthreshold electrocutaneous stimulation. Furthermore, the disclosed method and apparatus permit adjustment of the stimulation schedule, prolonging the slow wave sleep stage by preventing the patient from sub-awakening during the slow wave sleep stage. Further details and embodiments are discussed below.

DETAILED DESCRIPTION

Figure 1:
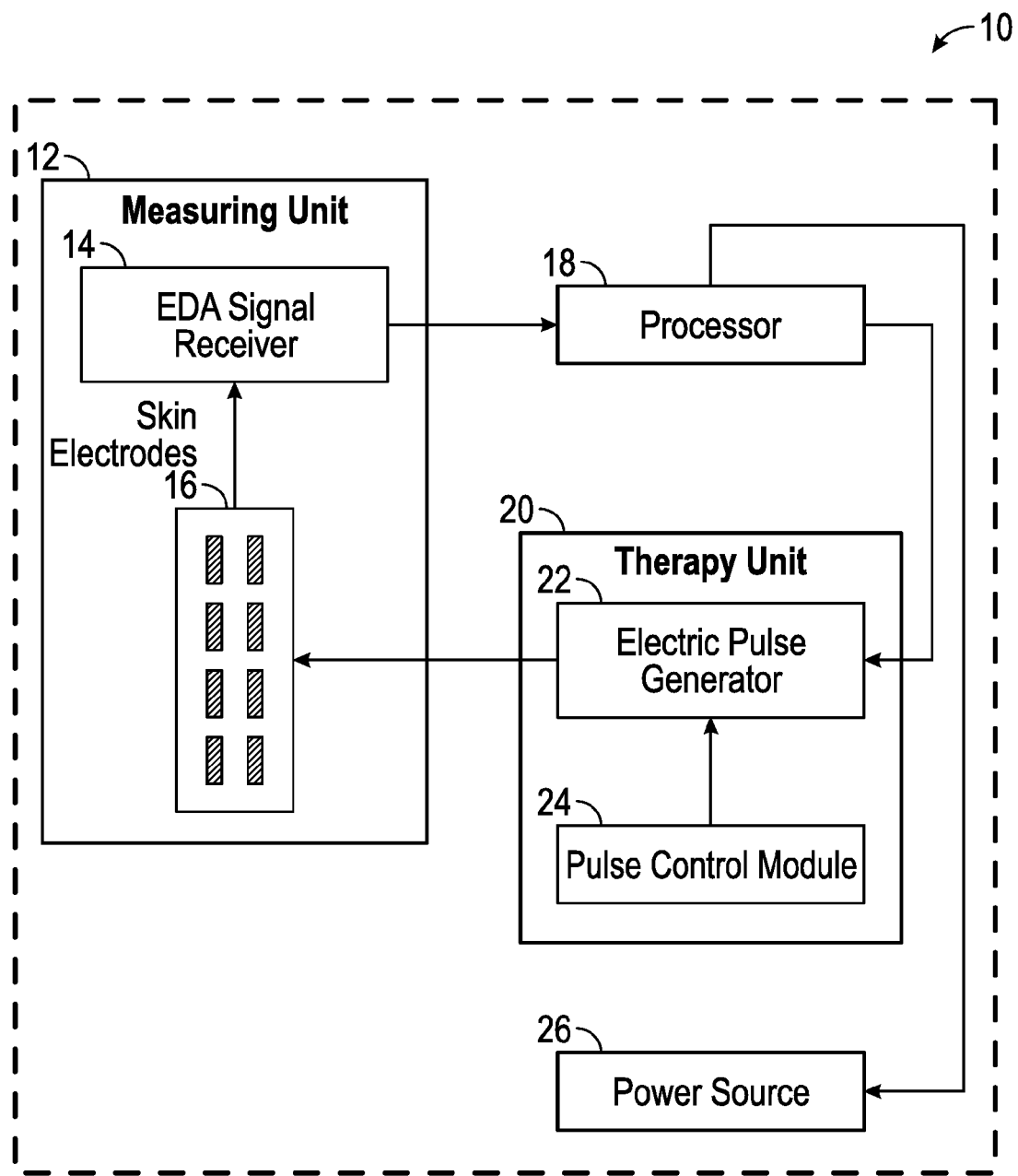
FIG. 1 is a functional block diagram illustrating components of an example threshold electrocutaneous stimulation apparatus that improves sleep architecture of patient.

A threshold electrocutaneous stimulation (TES) apparatus 10 that improves slow wave sleep stage of patient is shown schematically in FIG. 1. TES apparatus 10 includes measuring unit (MU) 12, therapy unit (TU) 20 and processer 18. In the example shown in FIG. 1, MU 12 includes an electrode system of eight skin electrodes 16 that are used to register the electrodermal activity (EDA) signal and apply subthreshold electrocutaneous stimulation. The MU 12 further includes an EDA signal receiver 14, which incorporates an electronic switch and amplifier (not shown). The electronic switch selectively connects each of 4 pairs of electrodes 16 to the amplifier for amplification of the EDA signal, where one of the two electrodes 16 in each pair of electrodes 16 may be neutral. The amplified signals are sent to an A/D converter for converting the analog EDA signal to a digital signal, which is sent to the processor 18 for analysis.

The TU 20 incorporates an electric pulse generator 22 for generating electric pulses and an electric pulse control module 24 for changing pulse parameters to deliver different schedules of subthreshold electrocutaneous stimulation therapy to the patient. The electric pulse generator 22 is controlled by the processor 18.

The processor 18 analyses the EDA signal and establishes whether the patient is in a slow wave sleep stage by determining the oscillation rate of the EDA signal. The processor 18 operates the TU 20 by switching on the pulse generator 22 in the onset of the slow wave sleep stage and then terminating the stimulation in the end of the slow wave stage. TES apparatus 10 also includes a replaceable power source 26 which is regulated by processor 18.

The TES apparatus 10 may be incorporated into a palm-sized (e.g. 2"×3") device connected to an adjustable band to position the electrodes 16 into contact with the skin on the user's palm, wrist, arm, etc.

The apparatus 10 has three functional modes: idle, active and stimulation.

Figure 2:
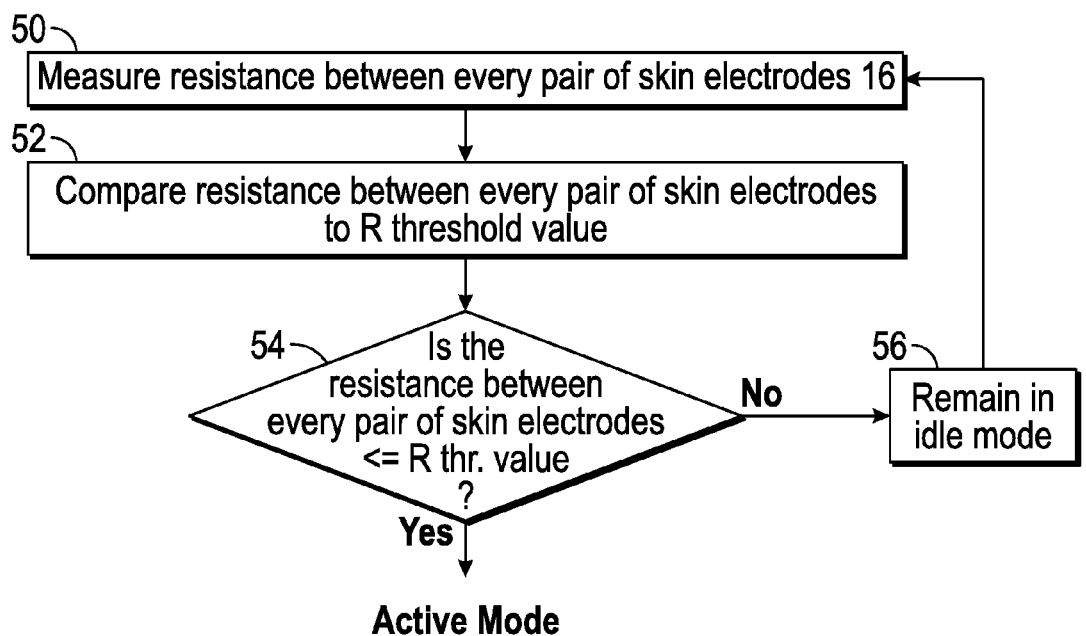
FIG. 2 shows flow diagrams illustrating example technique for operating the apparatus in the idle mode.

In the idle mode, the operational flow diagram of which is shown in FIG. 2, the processor 18 measures the skin resistance value R between each of 4 pairs of skin electrodes 16 in step 50. The processor 18 repeats the measurements every 5 seconds and compares the measured resistance value R to an R threshold value (e.g. 1 megohm) in step 52. In step 54, if the measured resistance value R is ≥R threshold value, the TES apparatus 10 remains in the idle mode with lowered power consumption in step 56. If the resistance value R is ≤R threshold value in step 54, that indicates that the galvanic contact between the skin and electrodes 16 (FIG. 1) is formed and the TES apparatus 10 switches to the active mode.

Figure 3:
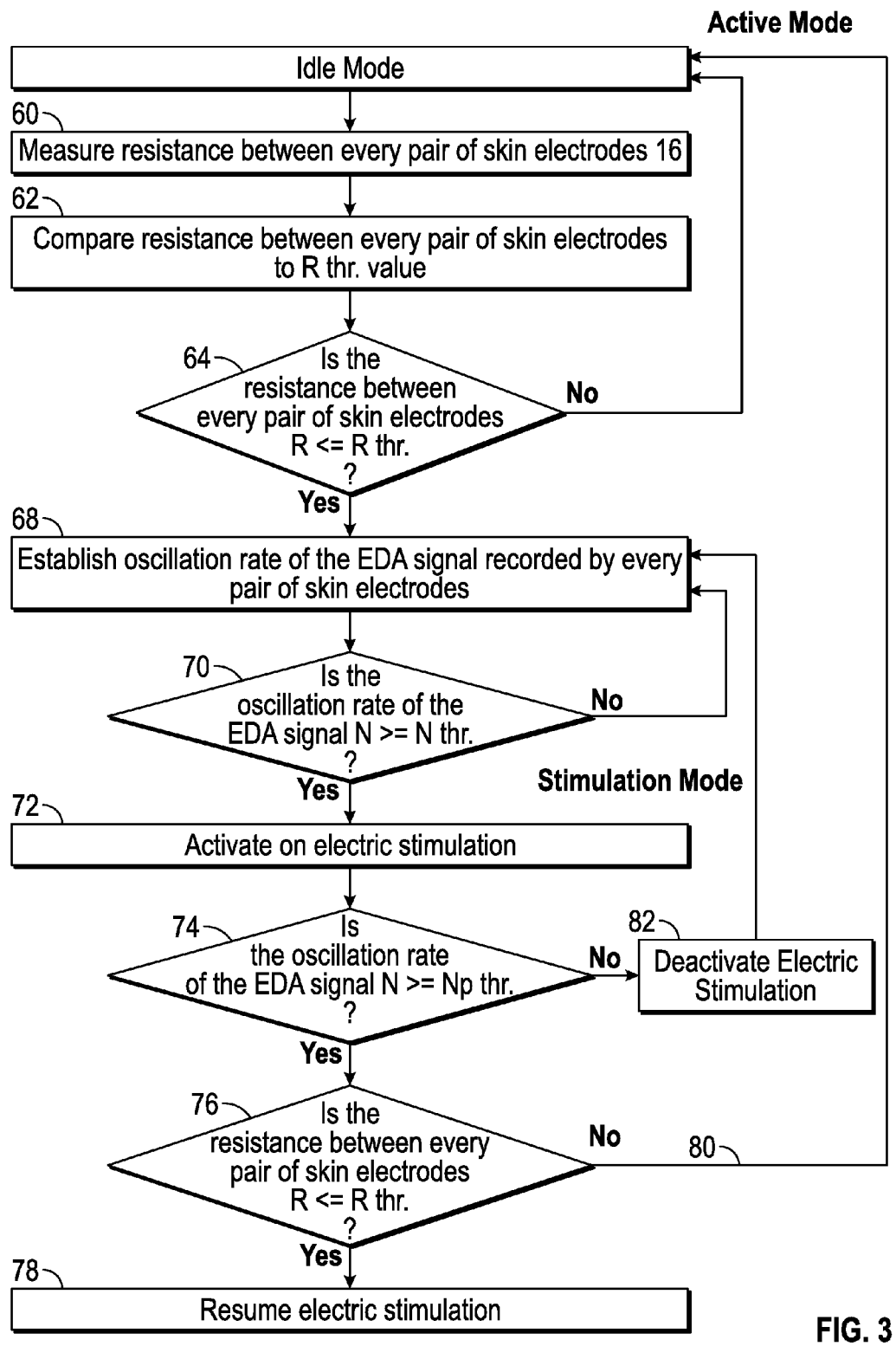
FIG. 3 shows flow diagrams illustrating example technique for operating the apparatus in the active mode.

The operational flow diagram of the active mode is shown in FIG. 3. In the active mode, the TES apparatus 10 measures the resistance value R between each of 4 pairs of skin electrodes 16 with a frequency of 10 Hz in step 60 and compares the resistance values R to a R threshold value in step 62. If the resistance value R between each of 4 pairs of skin electrodes remains ≤R threshold value in step 64, the EDA signal is analyzed by counting the number of oscillations N for every 60 second period in step 68. When the number of EDA signal oscillations reaches the rate of N threshold of 6 for a 60 second period in step 70, the TES apparatus 10 switches in the stimulation mode, otherwise the TES apparatus 10 keeps counting the number of EDA signal oscillations N for every 60 second period. If the resistance value R between any of 4 pairs of skin electrodes becomes ≥R threshold value, the TES apparatus 10 switches in the idle mode with a lowered power consumption.

In the stimulation mode the rectangular electric pulses are concurrently applied to each of 4 pairs of skin electrodes 16 (FIG. 1) in step 72. For example, the pulse current may be 100 microamps, pulse duration 10 milliseconds and pulse duty cycle 10^-2%. The electric stimulation period may last 30 seconds (for example). Afterwards, the stimulation pauses and the TES apparatus 10 switches into the pause measurement mode for 30 seconds, during which EDA signal is analyzed by counting the number of oscillations in step 74 and the resistance value R between each of 4 pairs of skin electrodes 16 is compared to the resistance values R to a R threshold value in step 76. If during the pause measurement mode the number of EDA signal oscillations N is ≥Np threshold value (such as 3) and the resistance value R between each of 4 pairs of skin electrodes remains ≤R threshold value, the TES apparatus 10 resumes electric stimulation of the patient in step 78. If the resistance value R between any of 4 pairs of skin electrodes becomes ≥R threshold value, the TES apparatus 10 switches in the idle mode with a lowered power consumption in step 80. If the number of EDA signal oscillations N is <Np threshold value of 3 (for example), the electric stimulation is terminated and TES apparatus 10 switches to the active mode in step 82. The Np threshold value could be between 0.5 to 20 oscillations per minute but is preferably between 3 to 10 oscillations per minute).

The subthreshold electrocutaneous stimulation therapy may include applying a rectangular pulse train or a rectangular pulse packet train to the skin area of the patient via the electrodes 16 (FIG. 1). The frequency of the rectangular pulse train may be between 0.1 Hz to 10 Hz. The frequency of the rectangular pulse train more preferably may be between 0.5 to 5 Hz. The frequency of the rectangular pulse packet train may be 0.1 Hz to 10 Hz. The frequency of the rectangular pulse packet envelope train more preferably may be between 0.5 to 5 Hz.

A rectangular pulse packet train comprises rectangular pulse packets. Each pulse packet comprises a series of rectangular pulses with identical frequency within the range of 500 Hz to 5,000 Hz. More preferably, the frequency may be in the range of 1,000 to 3,000 Hz. Each pulse packet may include a series of pulses with a given frequency distribution around a central frequency f. The series of rectangular pulses may have a desired frequency distribution within the pulse packet, such as Gaussian, Poisson, or Lorentz distribution.

The rectangular pulse train may include pulses in monopolar (unipolar), bipolar or combined unipolar-bipolar fashion. The rectangular pulse train parameters may include pulse amplitudes between 1 to 1,000 microamperes, more preferably from 50 to 500 microamperes, pulse durations between 1 to 500 milliseconds, more preferably from 1 to 100 milliseconds, and pulse periods between 0.1 to 3 seconds, more preferably from 0.5 to 1.5 seconds.

The rectangular pulse packet train may include pulse packets in monopolar (unipolar), bipolar or combined unipolar-bipolar fashion. The rectangular pulse packet train parameters include pulse packet amplitudes between 50 to 500 microamperes, pulse packet durations between 1 to 100 milliseconds, and pulse packet periods between 0.5 to 1.5 seconds.

Figure 4:
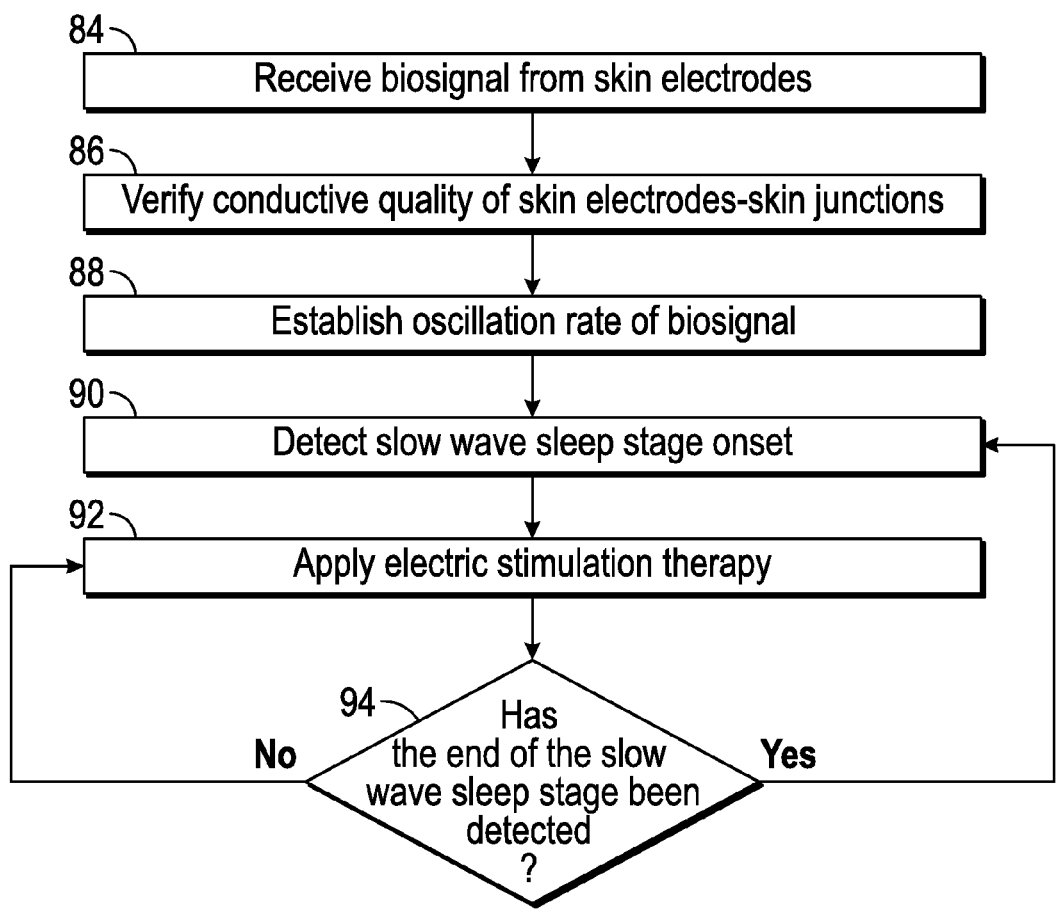
FIG. 4 shows flow diagrams illustrating example techniques for threshold electrocutaneous stimulation therapy delivery to a patient.

A flow diagram illustrating an example technique for subthreshold electrocutaneous stimulation therapy delivery to a patient is shown in FIG. 4. The biosignal (EDA signal) from skin electrodes 16 (FIG. 1) is received in step 82. The conductive quality of skin electrodes-skin junctions is verified in step 84. The oscillation rate of the biosignal is established in step 86. The slow wave sleep stage onset is detected in step 88. The electrostimulation therapy is then applied in step 90 upon the detection of the slow wave sleep stage onset in step 88. The electrostimulation therapy is applied during the slow wave sleep stage, until the slow wave stage end is detected in step 92. After that the electrostimulation therapy will resume only after the onset of the next slow wave sleep stage is detected.

The TES apparatus 10 may also include short-range wireless connectivity such as Bluetooth and/or Wi-Fi, for connecting to the user's device (e.g. smartphone, tablet, computer, docking station, etc). The TES apparatus 10 gathers information regarding the user's sleep patterns and sends this information to an app on the user's device. The app on the user's device can display the various sleep stages for each night's sleep, including the beginning and end times for each stage and the total and/or percentage time spent in each stage. The user may also send commands to the TES apparatus 10 with the app and device, such as adjusting different parameters, updating firmware, selectively disabling off the active mode (but continuing to monitor sleep stages), etc.

In accordance with the provisions of the patent statutes and jurisprudence, exemplary configurations described above are considered to represent a preferred embodiment of the invention. However, it should be noted that the invention can be practiced otherwise than as specifically illustrated and described without departing from its spirit or scope.

What is claimed is:

1. A method for improving sleep of a patient including the steps of:
    a) receiving a biosignal that is indicative of a sleep stage of the patient;
    b) establishing an oscillation rate characteristic of the biosignal;
    c) determining in a processor that the patient is in a slow wave sleep stage based on a determination that the oscillation rate characteristic of the biosignal exceeds a first threshold value, wherein the slow wave sleep stage occurs during a sleep state of the patient;
    d) applying electrocutaneous stimulation therapy based upon the determination in said step a) that the patient is in the slow wave sleep stage;
    e) after said step d), determining in the processor that the patient is no longer in the slow wave sleep stage, based upon an oscillation rate of the biosignal falling below a second threshold value lower than the first threshold value; and
    f) discontinuing the electrocutaneous stimulation therapy based upon the determination in said step e) that the patient is no longer in the slow wave sleep stage.

2. The method of claim 1 wherein said step d) further includes the steps of delivering said electrocutaneous stimulation therapy via skin electrodes to a skin area of the patient during the slow wave sleep stage based on an established slow wave sleep stage.

3. The method of claim 2 wherein the skin electrodes are used to register the biosignal and for applying the electrocutaneous stimulation therapy to the skin area of the patient.

4. The method of claim 2 wherein the biosignal includes an electrodermal activity value of the patient.

5. The method of claim 4 wherein the electrodermal activity value includes galvanic skin response, including skin conductance.

6. The method of claim 4 wherein said step b) further includes the steps of establishing an oscillation rate characteristic of the electrodermal activity value and said step c) includes determining the slow wave sleep stage of the patient based on the oscillation rate characteristic of the electrodermal activity value.

7. The method of claim 1 wherein the first threshold value of the oscillation rate characteristic of the oscillation rate is approximately 6 per 60 seconds.

8. The method of claim 1 further including the step of changing at least one therapy parameter value in the electrocutaneous stimulation therapy of said step d) based on the determination in said step c) that the patient is in the slow wave sleep stage.

9. The method of claim 1 wherein the electrocutaneous stimulation therapy includes applying a rectangular pulse train or a rectangular pulse packet train to a skin area of the patient.

10. The method of claim 9 wherein a frequency of the rectangular pulse train or the rectangular pulse packet train is between 0.1 Hz to 10 Hz.

11. The method of claim 10 wherein the frequency of the rectangular pulse train or the rectangular pulse packet train is between 0.5 to 5 Hz.

12. The method of claim 9 wherein, applying a rectangular pulse train or a rectangular pulse packet train comprises applying pulses in monopolar (unipolar), bipolar or combined unipolar-bipolar fashion.

13. The method of claim 1 further including the steps of applying the electrocutaneous stimulation therapy in said step d) based upon conductance of the skin exceeding a skin conductance threshold value, and discontinuing the electrocutaneous stimulation therapy in said step f) based upon the skin conductance falling below the skin conductance threshold value.

14. The method of claim 13 wherein the skin conductance threshold value is equal or less than 1 µS (microsiemens).

15. A method for improving sleep of a patient including the steps of:
   a) receiving a biosignal that is indicative of a sleep stage of the patient, establishing an oscillation rate characteristic of the biosignal, and determining in a processor that the patient is in a slow wave sleep stage based upon the oscillation rate characteristic of the biosignal of the patient;
   b) applying electrocutaneous stimulation therapy via skin electrodes to a skin area of the patient based upon the determination in said step a) that the patient is in the slow wave sleep stage, wherein the skin electrodes include a plurality of pairs of electrodes, where one of the two electrodes in each pair is neutral;
   c) after said step b), determining in the processor that the patient is no longer in the slow wave sleep stage; and
   d) discontinuing the electrocutaneous stimulation therapy based upon the determination in said step c) that the patient is no longer in the slow wave sleep stage.

16. A method for improving sleep of a patient including the steps of:
   a) determining in a processor that the patient is in a slow wave sleep stage based upon a determination that an oscillation rate characteristic of a biosignal of the patient exceeds a first threshold value;
   b) applying electrocutaneous stimulation therapy based upon the determination in said step a) that the patient is in the slow wave sleep stage, wherein the electrocutaneous stimulation therapy includes applying a rectangular pulse packet train to a skin area of the patient;
   c) after said step b), determining in the processor that the patient is no longer in the slow wave sleep stage; and
   d) discontinuing the electrocutaneous stimulation therapy based upon the determination in said step c) that the patient is no longer in the slow wave sleep stage, wherein the rectangular pulse packet train comprises rectangular pulse packets, wherein each pulse packet comprises a series of rectangular pulses with identical frequency within the range of 500 Hz to 5,000 Hz.

17. The method of claim 16 wherein the frequency is in the range of 1,000 to 3,000 Hz.

18. The method of claim 16, wherein each pulse packet comprises a series of pulses with a given frequency distribution around a central frequency.

19. A method for improving sleep of a patient including the steps of:
   a) determining in a processor that the patient is in a slow wave sleep stage based upon a determination that an oscillation rate characteristic of a biosignal of the patient exceeds a first threshold value;
   b) applying electrocutaneous stimulation therapy based upon the determination in said step a) that the patient is in the slow wave sleep stage, wherein the electrocutaneous stimulation therapy includes applying a rectangular pulse train or a rectangular pulse packet train to a skin area of the patient, and wherein the rectangular pulse train or the rectangular pulse packet train includes pulse amplitudes between 1 to 1,000 microamperes, pulse durations between 1 to 500 microseconds, and pulse periods between 0.1 to 3 seconds;
   c) after said step b), determining in the processor that the patient is no longer in the slow wave sleep stage; and
   d) discontinuing the electrocutaneous stimulation therapy based upon the determination in said step c) that the patient is no longer in the slow wave sleep stage.

20. The method of claim 19 wherein parameters of the rectangular pulse train or the rectangular pulse packet train include pulse amplitudes between 50 to 500 microamperes, pulse durations between 1 to 100 microseconds, and pulse periods between 0.5 to 1.5 seconds.

21. An apparatus comprising:
   a therapy unit configured to deliver electrocutaneous stimulation therapy to a skin area of a patient, the therapy unit including an electric pulse generator and a plurality of electrodes;
   a measuring unit configured to measure a biosignal representing electrodermal activity of the patient, the measuring unit including the plurality of electrodes;
   the plurality of electrodes configured to register the biosignal and to apply the electrocutaneous stimulation therapy to the skin area of the patient; and
   a processor configured to receive the biosignal from the measuring unit, to establish an oscillation rate of the biosignal, to establish a slow wave sleep stage of the patient based on the oscillation rate of the biosignal, wherein the slow wave sleep stage occurs during a sleep state of the patient, and to operate the therapy unit to deliver said electrocutaneous stimulation therapy to the skin area of the patient during the established slow wave sleep stage and to discontinue operation of the therapy unit when the patient is not in the established slow wave sleep stage, wherein the electrocutaneous stimulation therapy can be delivered and the biosignal can be measured with the plurality of electrodes.

22. The apparatus of claim 21 wherein the biosignal indicates electrodermal activity of the patient.

23. The apparatus of claim 21 wherein an oscillation rate characteristic comprises a number of pulses per minute of the biosignal.

24. The apparatus of claim 21, wherein the processor is configured to operate the therapy unit to deliver subthreshold electrocutaneous stimulation therapy to the skin area of the patient during the sleep state by activating the therapy unit based upon the biosignal oscillation rate exceeding a threshold value and deactivating the therapy unit based upon the biosignal oscillation rate falling below the threshold value.

25. The apparatus of claim 21 wherein the therapy unit is configured to deliver said electrocutaneous stimulation therapy by applying a rectangular pulse train or a rectangular pulse packet train to the skin area of the patient.

26. An apparatus comprising:
   a plurality of pairs of electrodes, wherein one of the two electrodes in each pair is neutral;
an electric pulse generator configured to deliver electrocutaneous stimulation therapy via the plurality of pairs of electrodes to a skin area of a patient;
   an electrodermal activity signal receiver connected to the plurality of pairs of electrodes;
and a processor configured to receive a biosignal representing electrodermal activity from the electrodermal activity signal receiver, to determine an oscillation rate of the biosignal, to determine a slow wave sleep stage of the patient based on the oscillation rate of the biosignal, and to operate the electric pulse generator to deliver said electrocutaneous stimulation therapy to the skin area of the patient during the slow wave sleep stage and to discontinue said electrocutaneous stimulation therapy based upon a determination that the patient is not in the slow wave sleep stage.

* * * * *